United States Patent [19]
Exner

[11] Patent Number: 6,051,434
[45] Date of Patent: *Apr. 18, 2000

[54] ACTIVATED PROTEIN C RESISTANCE TEST

[75] Inventor: Thomas Exner, Gordon, Australia

[73] Assignee: Gradipore Limited, North Ryde, Australia

[ * ] Notice: This patent issued on a continued prosecution application filed under 37 CFR 1.53(d), and is subject to the twenty year patent term provisions of 35 U.S.C. 154(a)(2).

[21] Appl. No.: 08/776,897

[22] PCT Filed: Aug. 7, 1995

[86] PCT No.: PCT/AU95/00474

§ 371 Date: Apr. 24, 1997

§ 102(e) Date: Apr. 24, 1997

[87] PCT Pub. No.: WO96/04560

PCT Pub. Date: Feb. 15, 1996

[30] Foreign Application Priority Data

Aug. 5, 1994 [AU] Australia ................................. PM7313

[51] Int. Cl.$^7$ .................................................. G01N 33/86
[52] U.S. Cl. ................................ 436/69; 436/63; 436/86; 436/164; 436/172; 436/174
[58] Field of Search ............................ 436/69, 86, 164, 436/172, 63, 174

[56] References Cited

U.S. PATENT DOCUMENTS

| | | | |
|---|---|---|---|
| 4,849,403 | 7/1989 | Stocker et al. | 514/2 |
| 5,342,830 | 8/1994 | Scarborough | 514/12 |
| 5,443,960 | 8/1995 | Dahlbäck | 435/13 |

FOREIGN PATENT DOCUMENTS 0 608 235 B1  1/1996  European Pat. Off. .
WO91/01382  2/1991  WIPO .

OTHER PUBLICATIONS

S. Schiffman et al, Biochemistry 1969, 8, 1397–1405.
D. Gowda et al, J. Biol. Chem. 1994, 269, 10644–10650.
K. Mertens et al. *Thromb. Haemostasis* 1985, 54, 650–653.
F. Franchi et al. *Thromb. Haemostasis* 1988, 60, 145–147.
T. Koster et al. *Lancet* 1993, 342, 1503–1506.
H. De Ronde et al. *Thromb. Haemostasis* 1994, 72, 880–886.
A.L. Babson et al. *Am. J. Clin. Pathol.* 1975, 64, 817–819.
K. Bergstrom et al. *Thromb. Res.* 1978, 12, 531–547.
M.C. Coots et al. *Am. J. Hematol.* 1979, 7, 173–180.

(List continued on next page.)

*Primary Examiner*—Arlen Soderquist
*Attorney, Agent, or Firm*—Michael J. Striker

[57] ABSTRACT

The method for determining functional activity of protein C in a human plasma sample includes incubating the human plasma sample with exogenous reagents that activate factor V and a common pathway of the blood coagulation mechanism through factor X, with activated exogenous protein C and with components that are necessary for efficient clotting of the human plasma sample, or incubating the human plasma sample with exogenous reagents that induce the presence of thrombin in a factor V dependent manner, with activated exogenous protein C and with components that are necessary for efficient clotting of the human plasma sample; monitoring a reaction indicative of a potential rate of coagulation of the plasma sample and comparing the resulting potential rate of coagulation with an equivalent rate for normal patient, or comparing the resulting potential rate of coagulation with an equivalent rate determined for the plasma sample in the absence of activated exogenous protein C; and determining the functional activity of the free protein C from this comparison.

11 Claims, 7 Drawing Sheets

OTHER PUBLICATIONS

F.J. Walker et al. *Biochemistry* 1980, 19, 1020–1023.
H.H. Salem et al. *Proc. Natl. Acad. Sci. USA* 1983, 80, 1584–1588.
K. Stocker et al. *Behring Inst. Mitt.* 1986, 79, 37–47.
P. Thiagarajan et al. *Blood,* 1986, 68, 869–874.
F. Espana et al. *Thromb. Res.* 1986, 44, 771–782.
C.A. Mitchell et al. *New. Eng. J. Med.* 1987, 317, 1638–1642.
T. Exner et al. *Thromb. Haemostasis* 1988, 59, 40–44.
L. Amer et al *Thromb. Res.* 1990, 57, 247–258.
T. Exner et al. *Blood Coagul. Fibrin.* 1990, 1, 259–266.
R.G. Malia et al *Br. J. Haematol.* 1990, 76, 101–107.
C. Ouyang et al *Adv. Exp. Med. Biol.* 1990, 281, 151–163.
H.A. Guglielmone et al. *Thromb. Haemostasis* 1992, 67 46–49.
B.M. Alving et al. *Thromb. Haemostasis* 1992, 67, 672–678.
I. Gerads et al. *Toxicon* 1992, 30, 1065–1079.
R. Schjetlein et al. *Thromb. Res.* 1993, 69, 239–250.
D.A. Triplett et al. *Thromb. Haemostasis* 1993, 70, 925–931.
R.A. Hutton et al. *Blood Rev.* 1993, 7, 176–189.
K. Stocker *Thromb. Haemostasis* 1994, 71, 257–260.
T. Exner *Blood Coagulat. Fibrin.* 1994, 5, 281–289.
N.A. Marsh *Blood Coagulat. Fibrin.* 1994, 5, 399–410.
T. Nakase et al. *Blood Coagulat. Fibrin.* 1994, 5, 173–177.
M. Bokarew et al. *Thromb. Res.* 1994, 75, 395–400.
R. M. Berting et al. *Nature,* 1994, 369, 64–67.
S. H. Jung et al. *Fish. Sci.* 1994, 60, 511–513.
M. Kraus et al. *Thromb. Res.* 1995, 80, 255–264.
B. Dahlbäck *Blood* 1995, 85, 607–614.
"An Experimental Approach to the Kinetics of Blood Coagulation", J. Margolis and Sally Bruce, Brit J. Haemat, 1964, 10, 513, pp. 513–529.
Patent Abstract: 5 472 852, Issued Dec. 5, 1995, Smirnov, et al.
Phosphatidylethanolamine Incorporation Into Vesicle Selective Enhances Factor VA Inactivation by Activated Protein C, Michael D. Smirnov & Charles T. Esmon, The Journal of Biological Chamistry vol. 289, No. 2, pp. 816–819, 1994.
"The Effect of Phospholipids, Calcium Ions and Protein S on Rate Constants of Human Factor VA Inactivation by Activated Human Protein C", Harry M. Bakker et al, J. Biochem. 208, pp. 171–178, 1992.
"The Mechanics of Inactivation of Human Factor V and Human Factor VA by Activated Protein C", Michael Kalafatis et al, The Journal of Biological Chemistry, vol., 269, No. 50, pp. 31869–31880, 1994.

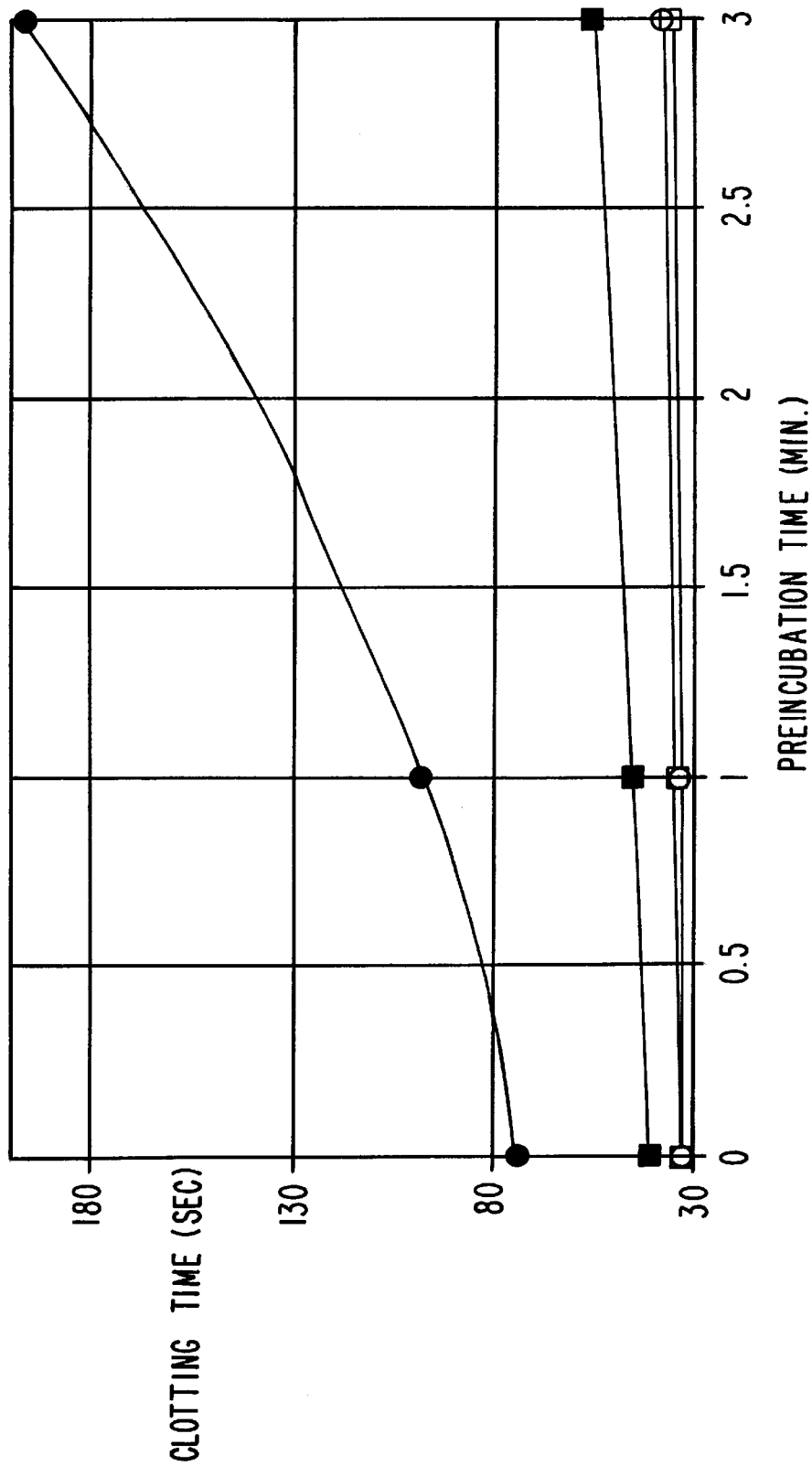

ACTIVATED PROTEIN C RESISTANCE TEST

FIELD OF THE INVENTION

The present invention relates to an improved test for protein C resistance in the blood coagulation system of patients.

BACKGROUND OF THE INVENTION

Known mechanisms for blood coagulation thrombosis and haemostasis are well described in International Patent Publication WO91/01382 the contents of which are incorporated herein by reference.

It is known from International Patent Publication WO93/01261, Bertina, R. M., Keulemans, B. P. C., Koster, T., et al, "Mutation in blood coagulation factor V associated with resistance to activated protein C", Nature 369, pp. 64 to 67 (1994) and Dahlback et al, "Inherited Thrombophilia: Resistance to activated protein C as a pathogenic factor of venous thromboembolism", Blood 85, pp. 607–614 (1995) that the risk of thrombosis in patients with a mutant factor V molecule known as the Leiden variant, or with activated protein C impairment for some other reason, may be determined by activating the coagulation system in a plasma sample and incubating the sample with activated protein C in what has come to be known as an activated protein C impairment, impedance or resistance test. There are precedents for this test in which impairment of activated protein C has been detected in patients with acquired thrombophilia (Mitchell et al, "Fatal thrombotic disorder associated with an acquired inhibitor of protein C", New England J. Med. 317, pp. 1638 to 1616 (1987) and Amer et al, "Impairment of the protein C anticoagulant pathway in a patient with systemic lupus erythematosus, anticardiolipin antibodies and thrombosis", Thromb. Res. 57, pp. 247–1990 (1988).

A substrate conversion reaction rate may be determined by the clotting time or by the time required for the conversion of a chromogenic substrate to a colored product. The conversion rate obtained is compared with values obtained in the absence of activated protein C and also with results for normal plasma samples. If the clotting time is not sufficiently prolonged by activated protein C, it indicates that the individual from which the sample is derived may be at a higher-than-normal risk of thrombosis.

SUMMARY OF THE INVENTION

According to the present invention if factor V is specifically activated by an exogenous reagent in addition to activation of the common pathway through factor X the test for activated protein C resistance may be made more sensitive and specific than previously known tests. According to the present invention a better specificity is obtained when a complex factor X activator is used together with the factor V activator. A similar result is achieved if prothrombin is activated to thrombin by a factor v dependent activator in the presence of a factor V activator.

The present invention consists in a method for determining the functional activity of protein C in a human plasma sample, comprising the steps of
(a) incubating the plasma sample with:
  (i) exogenous reagents which activate factor V and which activate the common pathway of the blood coagulation mechanism through factor X or by inducing the presence of thrombin in a factor V dependent manner,
  (ii) activated exogenous protein C, and
  (iii) components, such as phospholipid and calcium ions, that are necessary for efficient clotting of the plasma samples;
(b) monitoring a reaction indicative of the potential rate of coagulation of the plasma sample; and
(c) comparing the potential rate of coagulation measured in step (b) with the equivalent rate determined for a normal patient, or comparing the potential rate of coagulation measured in step (b) with the equivalent rate determined for the plasma sample in the absence of activated exogenous protein C, and determining the functional activity of the free protein C from one or the other of those comparisons.

In a preferred form of the invention the patient's plasma sample is pre-incubated with an exogenous activator for factor V prior to the initiation of clotting. The exogenous activators for both factors X and V are most preferably derived from snake venom. In one embodiment of the invention both the factor V and the factor X activators are derived from Russell's viper. The factor X activator is preferably derived from the venom of Russell's viper (*Vipera russelli*) and other immunologically cross-reactive species. A preferred factor V activator derives from *Naja nivea* and other immunologically cross-reactive species. The snake venoms may either be used in a diluted but unfractionated form which contributes to the simplicity of the test or, preferably, may be used in a fractionated form utilising isolated venom components.

Rather than directly activating factor X with an exogenous reagent one may also obtain an improvement over the known activated protein C test by utilising an exogenous reagent that induces in the plasma the presence of thrombin in a factor V dependent manner. In this aspect of the invention factor V dependent prothrombin activators such as those from certain Australian Notechis and Pseudonaja venoms, such as *Psudonaja textilis, Notechis scutatus* and *Ozyuranus scutellatus*, may be used. The use of this system bypasses factor X and all factors above it thereby making the test more specific than that based on Russell's viper venom alone. The use of additional venom-derived factor V activators is desirable exactly as described above for the Russell's viper venom activated system which involves factor X activation.

Addition to the incubation mixture of a factor v activator improves the sensitivity of the test. As used in this specification a factor V activator is taken to be a compound or material which activates factor V in a manner that makes it susceptible to degradation or deactivation by activated protein C. It is known that there are compounds which will cleave factor V in a way that renders it active but not in a form degradable by activated protein C. Such activators are not within the scope of this invention. The term activated protein C is taken to mean any compound having the functional activity of natural human activated protein C in degrading factor Va.

In the conventional APTT test and other currently used tests factor V is activated to FVa to a variable degree only by feedback from thrombin and factor Xa. These substances became present at a high level only near the clotting end point. In the method of the present invention factor V activation is a defined step induced by exogenous activator such as those derived from Russell's viper and from Naja (Cobra) venoms especially *Naja nivea*. Activated protein C destroys only activated factor V, not native factor V. As activated factor V is formed to a greater degree with the combination of activators present in this preferred form of the invention the test is more specific for activated protein C impedance caused by abnormal factor V.

It has recently been proposed that a major factor in activated protein C resistance is an abnormal factor V molecule which cannot be degraded by activated protein C. The importance of the present test can thus be seen in this genetic or hereditary condition. Moreover, it is clear that acquired resistance or impedance to activated protein C i.e., separate from inherited FV (Leiden), may be important in a number of clinical settings, including pregnancy, autoimmune diseases and lupus erythematosus, where antibodies may impair activated protein C function, and especially in combination with other thrombotic risk factors such as low protein S activity.

It is believed that the direct activation of factor X provides a surprising improvement over the known systems which typically are based on activated partial thromboplastin time (APTT) or prothrombin time (PT). In these known tests substantially the whole of the blood coagulation mechanism is stimulated either through the extrinsic or the intrinsic pathway. The present inventor has found that by the direct activation of factor X, particularly using snake venom derived factor X activators, and most particularly that found in Russell's viper venom and other immunologically cross-reactive species, the sensitivity of the test is improved. It is to be understood that in carrying out the invention it would be possible to merely add a factor V activator to an APTT or a PT-based activated protein C resistance test system. While this procedure is not particularly preferred it would yield the benefits of the present invention over prior art methods.

In one embodiment of the invention the components with which the patient's plasma are to be incubated are combined into a single mixture by the use of suitable surfactants, particularly non-ionic detergents. Such a single mixture preferably also contains supplemental components such as suitable buffers and preservatives. In addition the mixture preferably contains polybrene or another similar agent to reverse the effect of any heparin that may be present in the test samples. The incubation mixture preferably also contains relatively high levels of phospholipid at high ionic strength to overcome non-specific inhibitors such as lupus anticoagulants that may be present in the plasma sample.

Another complicating feature in test plasmas may be the defect caused by oral anticoagulants. Many such patients may already be on oral anticoagulant treatment which affects the clotting tests currently used to assess activated protein C resistance.

The conventional method for minimizing such interference, by mixing test plasmas with factor V deficient plasma, also works well with the Russell's viper venom (RVV) based activated protein C impedance method according to this invention. However, a more simple and less expensive method is preferred. To make the RVV-based activated protein C impedance test described here less affected by oral anticoagulant treatment, it is preferred to correct such defects by the inclusion of the vitamin K dependent clotting factors specifically depleted by such treatment. For the RVV-based test according to this invention, it is only necessary to include factors II, X and protein S. An example of a suitable source is the so-called Beriplex concentrate (Behringwerke, Germany). Addition of protein S is desirable to make the test more specific for activated protein C resistance due to factor V (Leiden) defect.

The method according to the present invention is preferably carried out as a 2-step or multistep procedure. This allows the possibility of investigating the mechanism of activated protein C resistance in a variety of clinical. conditions. In this case activated protein C is preincubated for 1–5 minutes with the test plasma in the optional presence of the factor V venom activator and supplementary clotting factors II, X and protein S. Immediately thereafter a clotting reagent, sensitive to the factor V level remaining, preferably a dilute RVV-based reagent, is added and the time to a clotting endpoint is determined. If the method according to the present invention is carried out as a multi-step incubation it would be possible to add exogenous protein C and an exogenous reagent which transforms protein C into activated protein C rather than adding activated protein C itself. It has been found that when the method is carried out using a single incubation mixture the calcium ions that must be present to induce blood clotting interfere with the activation of the exogenous protein C by the *A. Contortrix-*, and related species-, derived protein C activator, but not by the activation induced by the thrombin-thrombomodulin combination.

The detection system for monitoring the potential rates of change within the coagulation system may be a clotting time assay or a chromometric or fluorometric assay using an appropriate synthetic substrate. Such detection systems are well known and described in the patent specifications referred to in the introductory portions of this specification.

In order that the nature of the present invention may be more clearly understood, preferred forms thereof will be described with reference to the following examples and the accompanying drawings.

BRIEF DESCRIPTION OF THE DRAWINGS

FIG. 7 shows the effect of preincubating the activated protein C and factor V activator with normal and abnormal plasma prior to carrying out dilute RVV-based activated protein C resistance tests.

DESCRIPTION OF THE PREFERRED EMBODIMENTS AND BEST MODE OF THE INVENTION

Effect of Human APC on Various Tests

Activated human protein C (APC) (0.5–2 $\mu$g/ml) is mixed with factor V activator from *Naja nivea* venom (1–20 $\mu$g/ml) and then preincubated with an equal volume of test plasma for 1–5 min at 37° C. A prewarmed proprietary dilute Russell's viper venom-based reagent "LA-CONFIRM" (developed as a lupus anticoagulant resistant clotting time reagent and available from Gradipore Ltd., P.O. Box 1865, Macquarie Centre, North Ryde, NSW 2113, Australia) is then added to start the coagulation process. Comparative clotting tests are carried out in exactly the same way but without APC present and/or using pooled normal plasma.

All kit tests were carried out following the instructions of the manufacturers.

Figure 1:
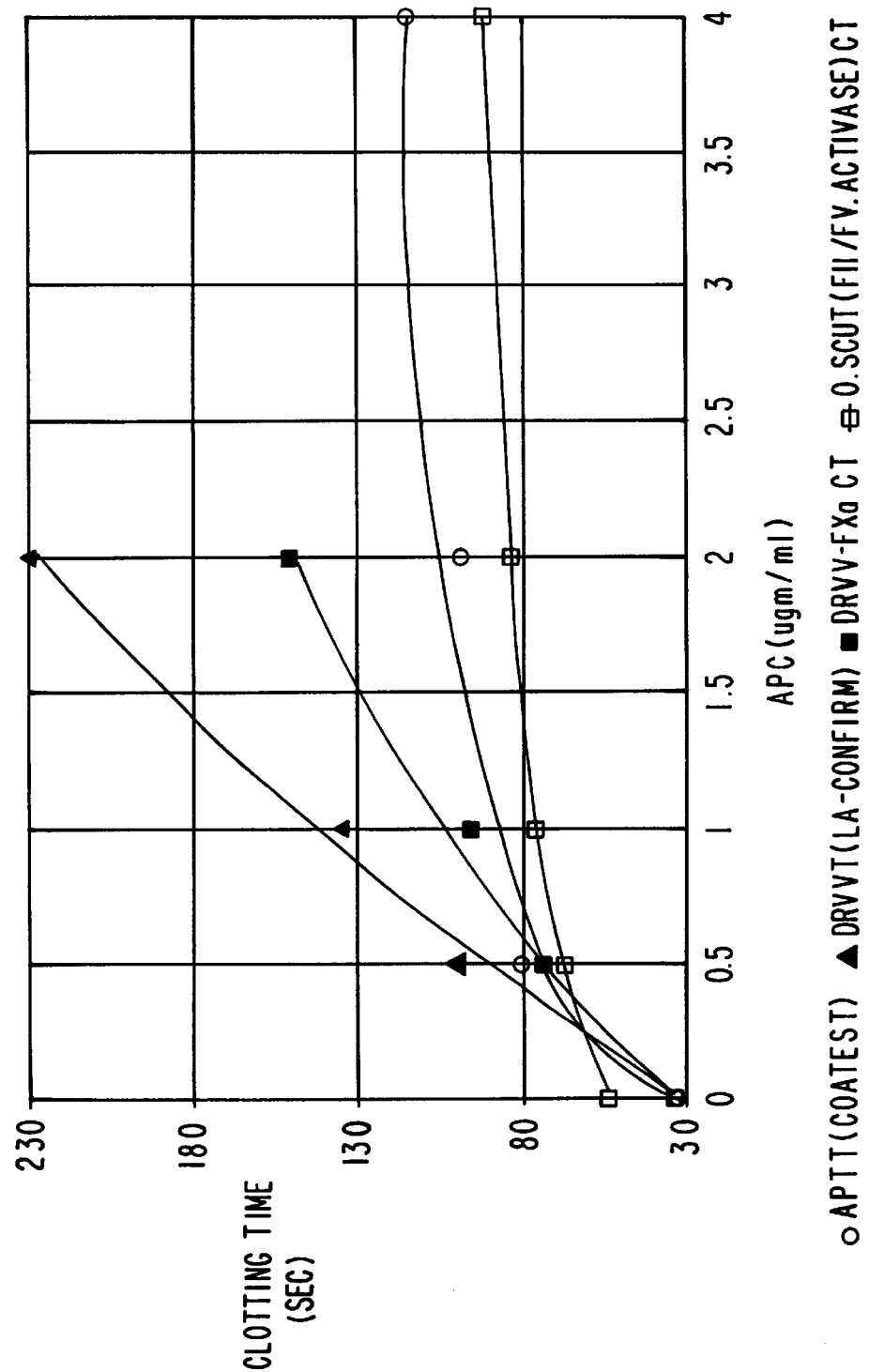
FIG. 1 shows the effect of human activated protein C on a number of clotting tests.

The effect of varying APC concentrations in several tests for APC resistance is shown in FIG. 1. In each case the clotting times were determined on pooled normal human plasma. The index tests were carried out using COATEST-APTT reagent specifically used in the APC-resistance kit marketed by CHROMOGENEX and made according to Australian Patent Application 21980/92. Pure human APC from Haematologic Technologies Inc, USA was added to the calcium chloride used in this test. The APTT prolonged in a non-linear fashion, not exceeding 120 sec even with 4 $\mu$g/ml APC present.

When APC was added to DRVVT (LA-CONFIRM) a much more linear response was obtained (FIG. 1) and the clotting time exceeded 150 sec with less than 2 $\mu$g/ml APC. When the DRVVT reagent was modified to contain only the factor X activator isolated from Russell's viper venom (RVVFXa CT)(obtained from American Diagnostica Inc, USA and not containing the factor V activator) a reduced sensitivity to APC was obtained. This clearly shows that factor V activation by the crude Russell's viper venom improves the sensitivity to APC and is a desirable component of the test system.

The identical test based on *Oxyuranus Scutellatus* (Taipan) venom (OXYURA/CT) at a concentration of $5\times10^{-6}$%w/v added to the LA-CONFIRM formula devoid of Russell's viper venom showed prolongation by APC though less than that induced in either the APTT or DRVV-based tests.

Comparison of Various APC Resistance Tests

Figure 2:
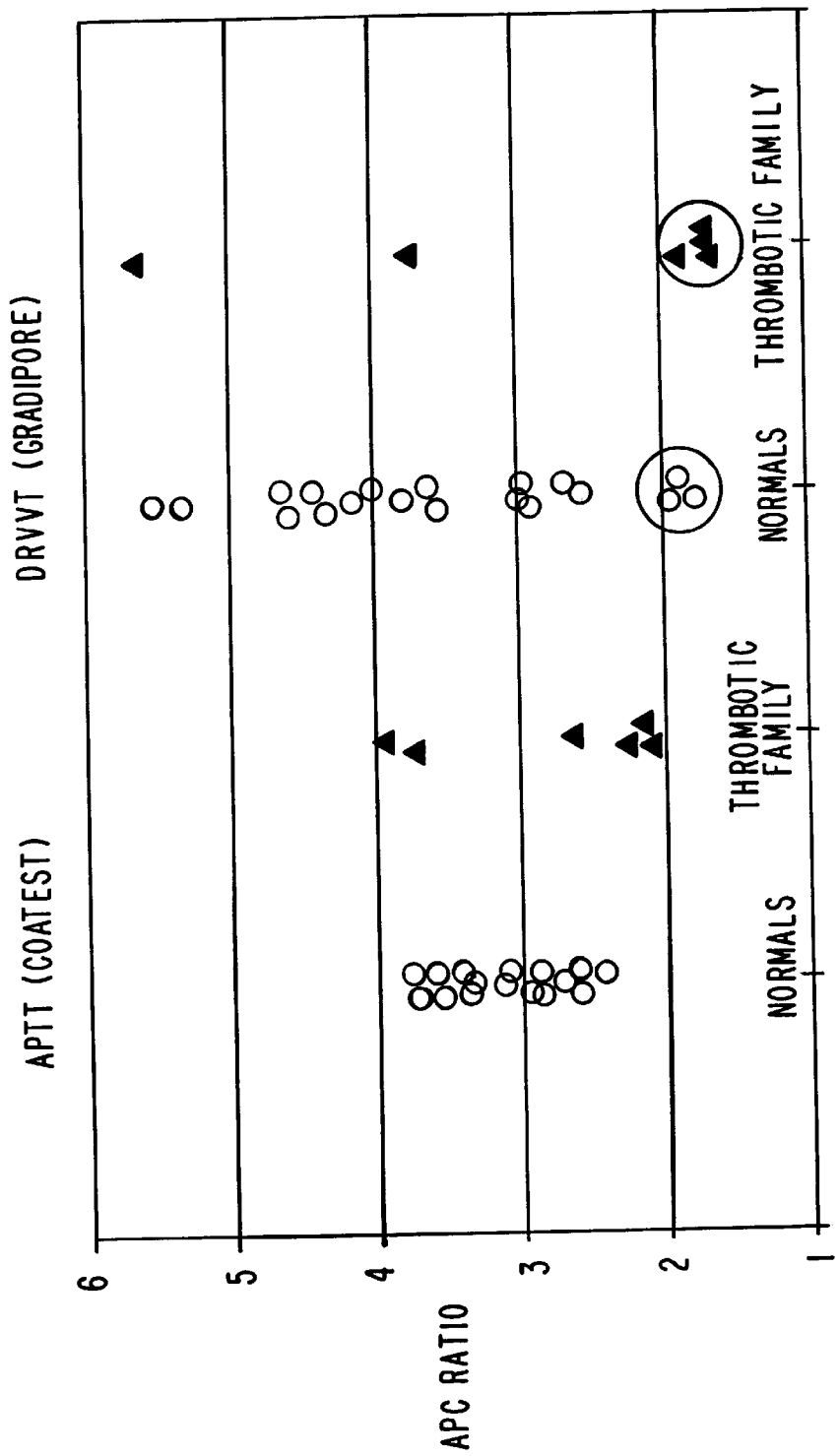
FIG. 2 shows a comparison of traditional APTT-based activated protein C with that based on the method according to this invention on a number of patient samples.

Six members of a family believed to have familial thrombophilia were tested with the dilute Russell's viper venom-based APC resistance test in comparison with the Coatest APTT-based method. Results expressed as APC resistance ratios are shown in FIG. 2 in comparison with various normal healthy blood donors. No individuals appeared to be abnormal using the Coatest method and a cut-off of 2.0. The DRVVT-based method, however, revealed that 4 of the 6 family members were clearly abnormal. Also 3 of the 19 normal individuals appeared abnormal with this test. The abnormal results are circled in FIG. 2. DNA analysis of all of the apparently abnormal individuals subsequently confirmed the presence of an arginine 506 to glutamine mutation, conferring APC resistance i.e. the Leiden factor V deficiency. The lower APC resistance ratios in affected members determined with the DRVVT-based test relative to mean normal clearly shows it to be a more sensitive test than the APTT-based Coatest method.

Methodology

Figure 3:
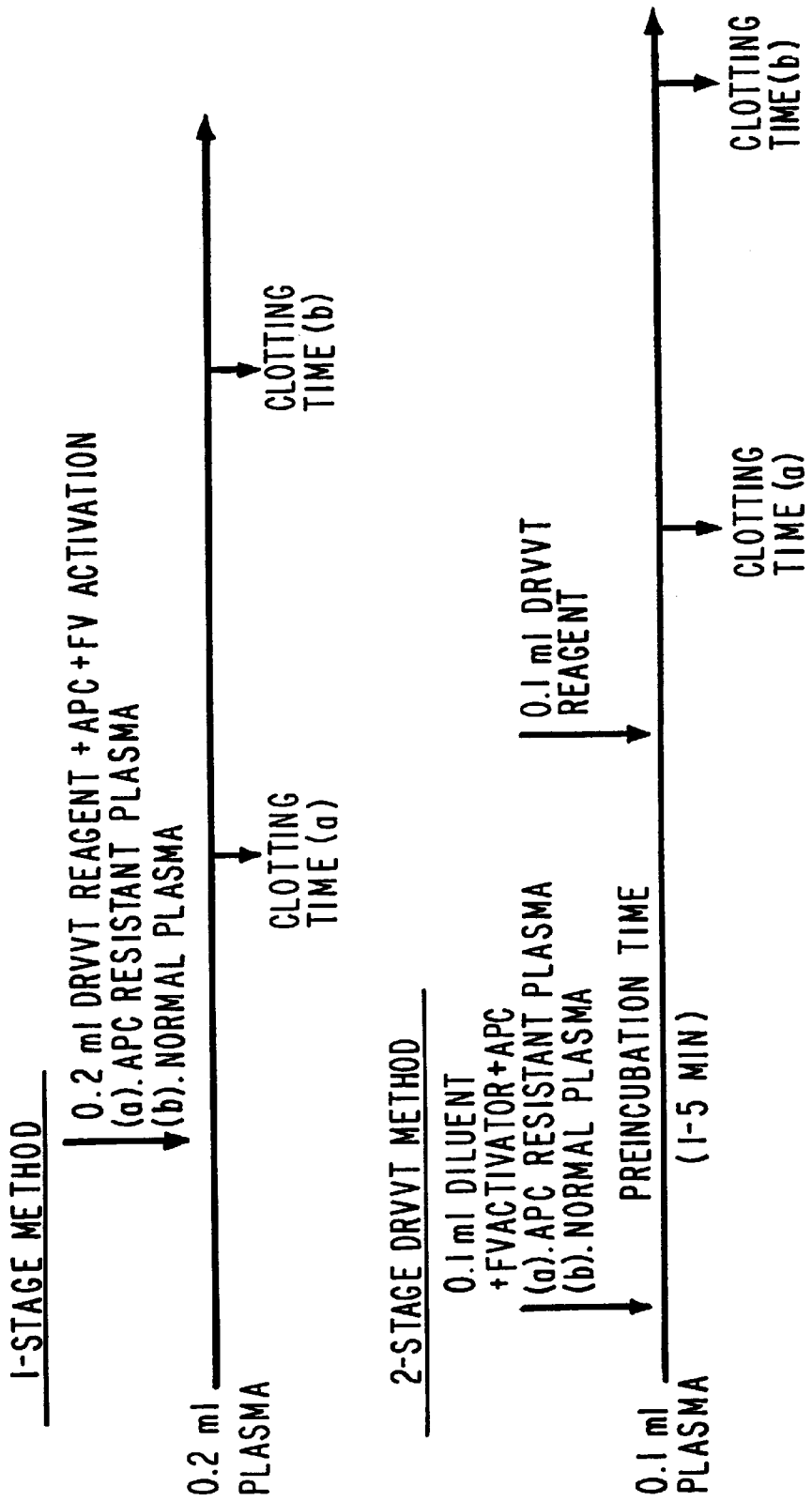
FIG. 3 shows an outline of the one and two stage methodologies for a method according to the present invention.

The initially-described one-stage method in which APC was premixed with the DRVVT reagent is shown schematically in FIG. 3. The mixed reagent showed some instability especially at room temperature and a 2-stage method was devised (FIG. 3). Method is added separately from the DRVVT reagent. The APC reagent has been found in this case to be more stable. The APC is preferably mixed with a factor V activator derived from Naja venoms in the same schematic diagram. The method resembles a traditional APTT format and is thus easily adaptable for automation.

Comparison of 1- and 2-Stage DRVVT Tests for APC Resistance

Figure 4:
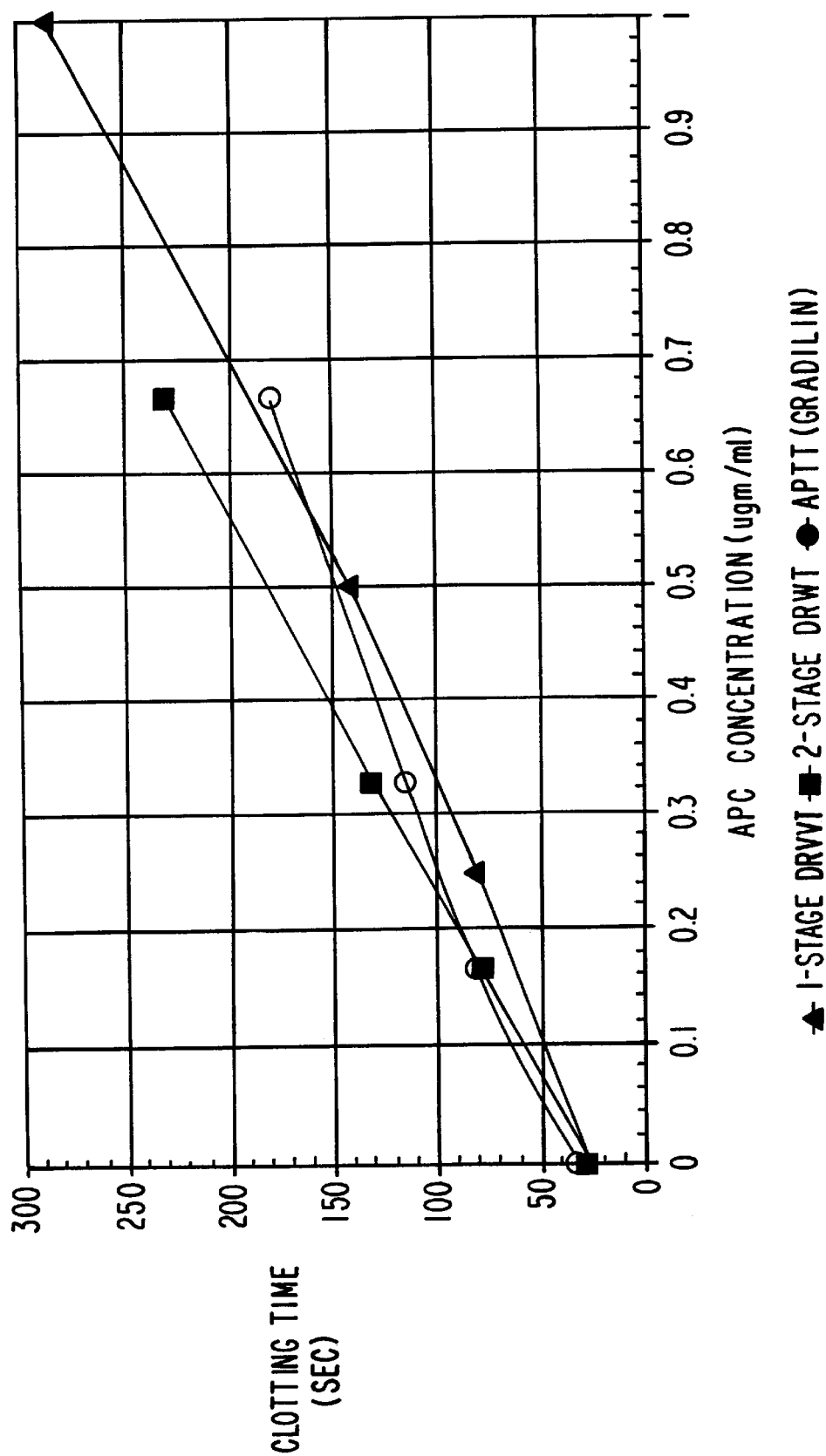
FIG. 4 shows the relative sensitivities of one and two stage dilute DRVV tests according to this invention for activated protein C.

Fortuitously it was found that the 2-stage method was more sensitive to APC concentration, expressed in FIG. 4 as the level of APC in the final clotting mixture volume. Numerous other studies have shown that the 2-stage method provided similar discrimination of FV (Leiden) subjects from normal while being technically more reliable. In the procedure illustrated in FIG. 3 factor V activator can be added with the APC or at any earlier stage to enhance this discrimination (with less APC being required for similar long clotting times among normals). Thus the two stage method is most sensitive to activated protein C and this is even more enhanced when an additional venom FV activator is included.

Screening for FV Activators

Figure 5:
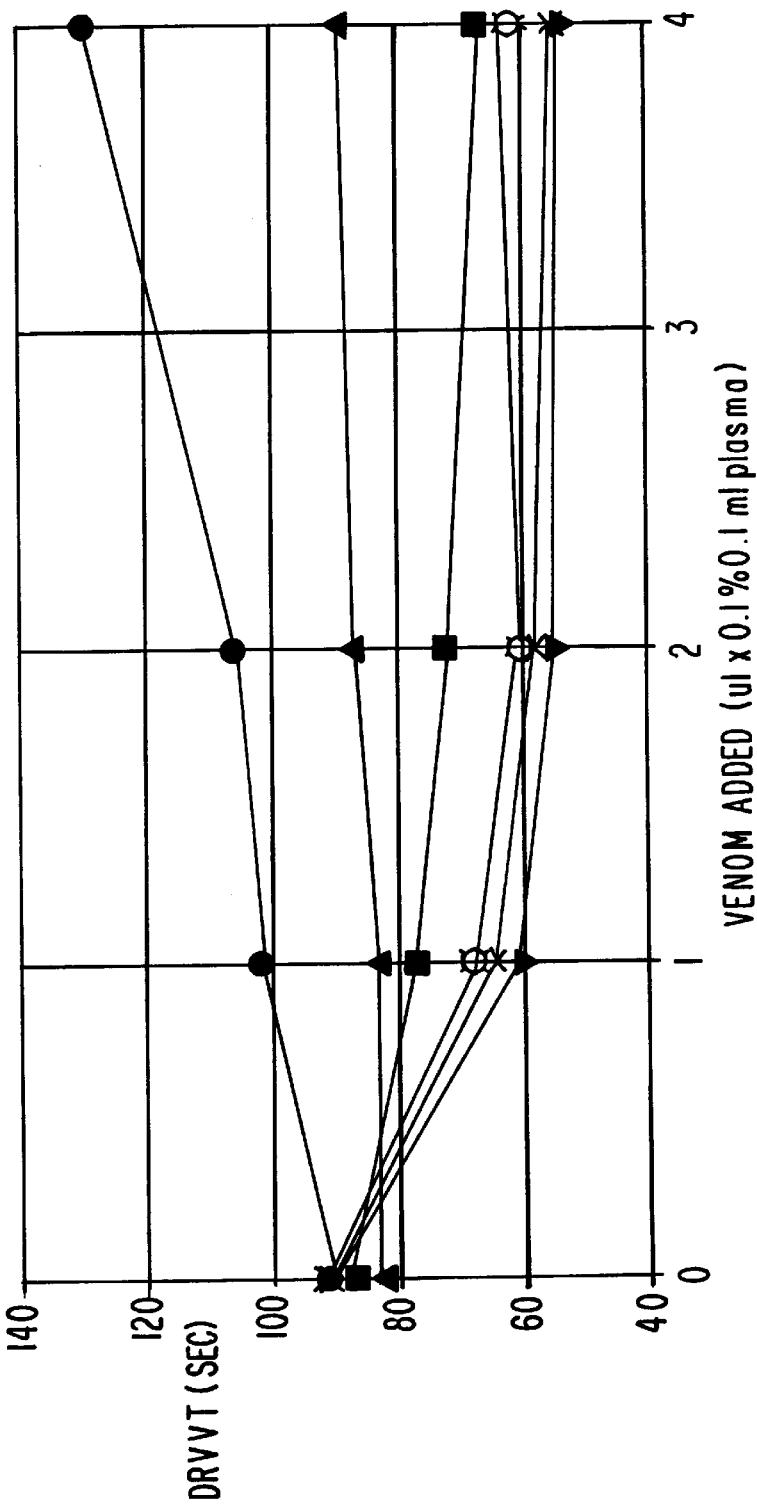
FIG. 5 shows screening tests for factor V activators among a number of crude snake venoms.

Crude venoms often contain procoagulants complicating the search for anticoagulant components. FIG. 5 shows the effect of various Elapid venoms reported to contain factor V activators on an APC resistance test (Gerads et. al, "Activation of bovine factor V by an activator purified from the venom of *Naja oxiana*", Toxicon. 30, pp. 1065 to 1079, (1992). Most of these shortened the clotting time due to exogenous activators of coagulation. Significant activated protein C enhancing activity, presumably due to factor V activator, was detectable in unfractionated *Naja nivea* venom. *Naja nivea* solutions prolonged LA-CONFIRM results on normal plasma in the presence of APC suggesting that a factor V activator, stimulating factor Va inactivation by APC, may have been present. This venom was fractionated by gel filtration. It is expected that fractionation of the other venoms would reveal components which could act as FV activators for use in the present invention.

Gel Filtration

Figure 6:
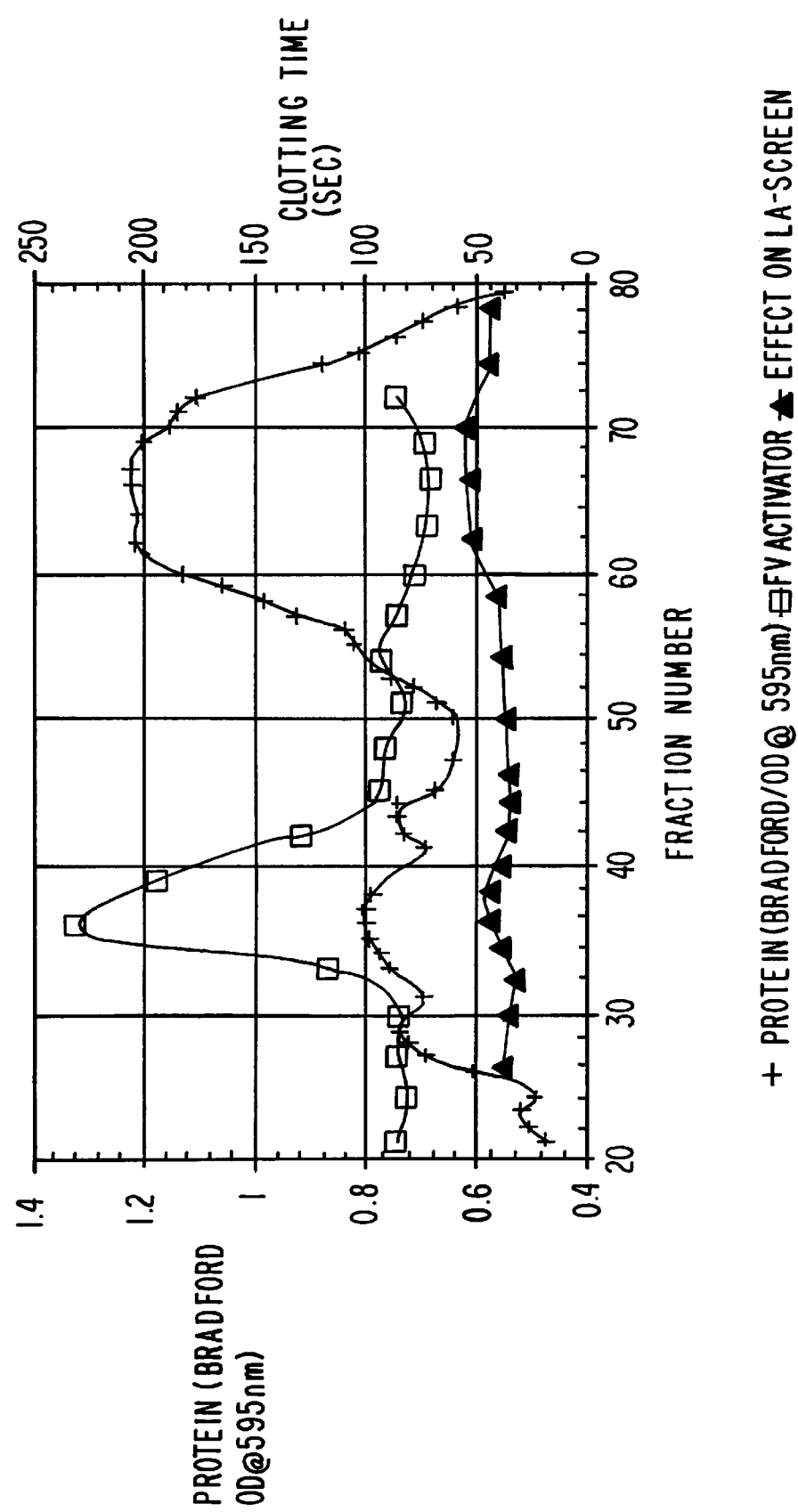
FIG. 6 shows gel filtration studies of *Naja nivea* venom.

Gel filtration of *Naja nivea* venom on Sephadex G, 50 and testing of factors confirmed the presence of a powerful APC-enhancing component. As shown in FIG. 6 the peak anticoagulant activity occurred at fraction number 37. Analysis by SDS—polyacrylamide gel electrophoresis revealed a main protein band at 60,000±10,000 molecular weight.

Mechanism of the APC-Enhancing Activity

FIG. 7 shows the effect of varying the preincubation time for a venom factor V activator (fraction 37) derived from *Naja nivea* with pooled normal plasma (PNP) and abnormal plasma (ABN) derived from a patient with the FV Leiden genetic trait both with activated protein C (+APC) and without activated protein C (−APC). The preincubated plasma were then tested for clotting time using a DRVVT-based APC in a time dependent manner and resistance test. These results confirm that the factor V activator from *Naja nivea* venom enhances the sensitivity of normal plasma to prolongation by APC in a time dependent manner and to a much greater degree than with factor V (Leiden) plasma.

I claim:

1. A method of determining functional activity of protein C in a human plasma sample, said method comprising the steps of:

a) incubating the human plasma sample with an exogenous reagent, activated exogenous protein C and components necessary for clotting of the human plasma sample, wherein said exogenous reagent either activates factor V and the common pathway of the blood coagulation mechanism through factor X by directly activating said factor X and said exogenous reagent is derived from *Vipera russelli* snake venom; or said exogenous reagent induces the presence of thrombin in a factor-V-dependent manner and is derived from *Vipera russelli* snake venom;

b) monitoring a reaction indicative of the rate of coagulation of the human plasma sample;

c) comparing the rate of coagulation determined in step b) with an equivalent rate of coagulation for a normal subject, or comparing the rate of coagulation determined in step b) with an equivalent rate of coagulation determined for the human plasma sample in the absence of the activated exogenous protein C; and d) determining the functional activity of the free protein C from the comparing of step c).

2. The method as defined in claim 1, wherein the human plasma sample is pre-incubated with an exogenous activator for said factor V prior to initiating said coagulation.

3. The method as defined in claim 1, wherein said human plasma sample is pre-incubated with an exogenous activator for said factor V and/or said activated exogenous protein C for one to five minutes prior to initiating said coagulation.

4. The method as defined in claim 1, wherein said exogenous reagent induces the presence of said thrombin in said factor-V-dependent manner so as to activate the common pathway of the blood coagulation mechanism.

5. The method as defined in claim 1, wherein said components necessary for clotting comprise phospholipids and calcium ions.

6. The method as defined in claim 1, wherein the human plasma sample or the activated exogenous protein C is incubated with at least one exogenous vitamin K dependent clotting factor to supplement said at least one exogenous vitamin K dependent clotting factor depleted in a patient by oral anti-coagulation treatment.

7. The method as defined in claim 6, wherein said at least one exogenous vitamin K dependent clotting factor is factor II, factor X, protein S or a mixture thereof.

8. The method as defined in claim 1, wherein the functional activity of the protein C is determined by comparing the rate of coagulation determined in step b) with the equivalent rate of coagulation for the normal subject.

9. The method as defined in claim 1, wherein said reaction monitored to indicate the rate of coagulation of the human plasma sample is the actual plasma clotting time.

10. The method as defined in claim 1, wherein said reaction monitored to indicate the rate of coagulation of the human plasma sample is conversion of a chromometric or fluorometric substrate by an enzyme generated through the clotting process.

11. The method as defined in claim 1, wherein the human plasma sample is incubated with phospholipids at high ionic strength to neutralize or overcome lupus anticoagulants.

* * * * *